United States Patent [19]

Lopez et al.

[11] Patent Number: 5,932,193
[45] Date of Patent: Aug. 3, 1999

[54] TOOTHPASTE COMPOSITIONS CONTAINING FLUIDIZED POLYMER SUSPENSIONS OF CARBOXYMETHYL CELLULOSE

[75] Inventors: Jean-Paul Lopez, Villemomble, France; Mohand Melbouci, Dordrecht, Netherlands; Gerhard Dewald, Obereisesheim, Germany

[73] Assignee: Hercules Incorporated, Wilmington, Del.

[21] Appl. No.: 08/935,711

[22] Filed: Sep. 23, 1997

Related U.S. Application Data

[63] Continuation of application No. 08/660,310, Jun. 7, 1996, abandoned.

[51] Int. Cl.$^6$ .............................. A61K 7/18; A61K 7/16; A61K 7/24
[52] U.S. Cl. .............................. 424/52; 424/55; 424/49; 424/50; 424/51; 424/53; 424/54; 424/56; 514/781; 514/835
[58] Field of Search .................... 514/781, 835; 424/52, 55, 49–56

[56] References Cited

U.S. PATENT DOCUMENTS

| | | | |
|---|---|---|---|
| 3,574,824 | 4/1971 | Echeaudia et al. ................... | 424/50 |
| 4,312,675 | 1/1982 | Pickens et al. ..................... | 106/171 |
| 4,325,861 | 4/1982 | Braun et al. ....................... | 523/205 |
| 4,485,089 | 11/1984 | Leipold ............................. | 424/49 |
| 4,585,812 | 4/1986 | Field ............................... | 523/221 |
| 4,799,962 | 1/1989 | Ahmed .............................. | 106/188 |
| 5,071,638 | 12/1991 | Yoshie et al. ...................... | 424/49 |
| 5,094,843 | 3/1992 | Mazzanobile et al. ................ | 424/52 |
| 5,192,529 | 3/1993 | Garlick, Jr. et al. ................ | 424/49 |
| 5,474,761 | 12/1995 | Liang .............................. | 424/52 |
| 5,487,777 | 1/1996 | Lundan et al. ..................... | 106/188 |
| 5,500,206 | 3/1996 | Charbonneau ....................... | 424/50 |
| 5,578,295 | 11/1996 | Francis et al. ..................... | 424/57 |
| 5,601,803 | 2/1997 | Masters et al. ..................... | 474/49 |

FOREIGN PATENT DOCUMENTS

| | | |
|---|---|---|
| 1363182 | 8/1972 | United Kingdom . |
| WO93/20139 | 10/1993 | WIPO . |

OTHER PUBLICATIONS

Chemical Abstracts 75:143998, 1969.
Chemical Abstracts 102:168703, 1984.
Chemical Abstracts 110:121131, 1988.
Chemical Abstracts 116:66968, 1991.
Chemical Abstracts 123:296295, 1995.
Chemical Abstracts 111:140504, 1989.
Chemical Abstracts 115:78936, 1991.

*Primary Examiner*—Alan L. Rotman
*Assistant Examiner*—D. Margaret M. Mach
*Attorney, Agent, or Firm*—Martin F. Sloan

[57] ABSTRACT

Disclosed are toothpaste compositions and a process for preparing such compositions comprising dental abrasive, humectant, fluidized polymer suspension and a suitable vehicle for the humectant, wherein the fluidized polymer suspension comprises: polyethylene glycol, carboxymethyl cellulose and hydrated thickening silica.

31 Claims, No Drawings

TOOTHPASTE COMPOSITIONS CONTAINING FLUIDIZED POLYMER SUSPENSIONS OF CARBOXYMETHYL CELLULOSE

This is a continuation of application Ser. No. 08/660,310, filed Jun. 7, 1996 now abandoned.

FIELD OF THE INVENTION

This invention relates to toothpaste compositions containing fluidized polymer suspensions of carboxymethyl cellulose and to methods for preparing said toothpaste compositions.

BACKGROUND OF THE INVENTION

Toothpaste formulations generally contain dentally acceptable abrasive, humectant, water, and water-soluble polymer which serves as a thickener and binder for the ingredients. A variety of other ingredients such as flavors, sweeteners, preservatives and fluoride are also utilized at low levels. Glycerin and sorbitol are the most commonly used humectants for toothpaste, and depending on the characteristics desired in the product, polyethylene glycol or polypropylene glycol may be incorporated as well. Two types of toothpaste are widely produced: 1) cream or opaque; and 2) transparent or translucent gel.

The most commonly used thickeners or binders for toothpaste are carboxymethyl cellulose (CMC) and hydroxyethyl cellulose (HEC). Carrageenan, xanthan and polyacrylates are also used, but much less widely.

In the manufacturing process for toothpastes, incorporation of the dry water-soluble binder polymer into the composition often presents difficulties because of the tendency for lump formation when the dry polymers are added to and dispersed in aqueous systems. Attempts to avoid this problem have resulted in several typical procedures for toothpaste manufacture. In the first, the binder is predispersed in a non-solvent (glycerin is preferred to wet out the binder), and then a sorbitol/water mixture is added with vigorous agitation. If there is no (or only a low level of) glycerin or other water-miscible organic liquid in the formulation, then all the available sorbitol is used with as much free water as possible with vigorous agitation. In the second method, the binder is dry blended with other dry materials in the formulation, e.g. abrasive, and then the resulting blend is dispersed in the liquid ingredients with strong agitation. To obtain a good dispersion the binder should be less than about 20% of the total dry blend. In this method it is important to avoid blending the binder with materials that compete for water, e.g., salts or sweeteners.

These dispersion techniques are very time consuming. Consequently, there is a need in the industry for methods of incorporating water-soluble binder polymers which lead to lump-free products, rapid viscosity development and reduced batch preparation time, and which allow convenient handling of the binder.

U.S. Pat. No. 3,574,824 discloses an anhydrous toothpaste base having the following ingredients: an oil, such as mineral oil or vegetable oil, with a viscosity of 100 to 300 cps; a combination of polyethylene glycols having a viscosity of 2,200 to 3,400 cps with molecular weights of 550 to 6,000; a non-toxic and non-ionic emulsifier; at least one binding agent; and a compound having a negative heat of hydration. Binding agents disclosed are polyvinylpyrrolidone, colloidal magnesium aluminum silicate, gum acacia, sodium alginate, extract of Irish moss, carboxymethyl cellulose and methyl cellulose. Hexahydric alcohols, in particular mannitol and inositol, are disclosed as compounds having a negative heat of hydration.

U.S. Pat. No. 5,192,529 teaches a dentifrice composition that contains a polyol humectant, abrasive, and a thickener system consisting of low viscosity sodium carboxymethyl cellulose and low viscosity hydroxyethyl cellulose.

U.K. Patent No. 1,363,182 discloses a transparent or translucent gel toothpaste composition comprising polyethylene glycol having molecular weight below 700, and hydrated silica gel polishing agent having a specific surface area below 600 $m^2/g$. The composition may be thickened with carboxymethyl cellulose.

None of the aforementioned references discloses the use of fluidized polymer suspensions in toothpastes.

SUMMARY OF THE INVENTION

This invention relates to toothpaste compositions comprising dental abrasive, humectant and fluidized polymer suspension, wherein the fluidized polymer suspension comprises polyethylene glycol, carboxymethyl cellulose and hydrated thickening silica. In preferred compositions the humectant is glycerin, sorbitol, polyethylene glycol, propylene glycol, or mixtures thereof.

In another embodiment, the invention relates to an improved process for preparing a toothpaste composition comprising dry carboxymethyl cellulose, the improvement comprising substituting for the dry carboxymethyl cellulose a fluidized polymer suspension comprising polyethylene glycol, carboxymethyl cellulose and hydrated thickening silica, whereby the carboxymethyl cellulose present in the fluidized polymer suspension dissolves in the composition in a shorter time than does the dry carboxymethyl cellulose.

DETAILED DESCRIPTION OF THE INVENTION

The present invention relates to toothpaste compositions containing dental abrasive, humectant, and fluidized polymer suspension. The fluidized polymer suspensions comprise polyethylene glycol, carboxymethyl cellulose and hydrated thickening silica. The toothpaste compositions may further contain water or other vehicles for the humectant, and encompass both opaque or cream, and transparent or translucent compositions.

The use of carboxymethyl cellulose as a fluidized polymer suspension in the toothpastes of the present invention, provides a substantial advantage over the use of dry polymer, because the suspensions eliminate the problems of lumping and slow dispersion when dry polymer is used. That is, the water-soluble polymer dissolves in the composition in a shorter time when it is in the form of fluidized polymer suspension than when it is in the form of dry polymer.

The fluidized polymer suspensions of this invention comprise suspensions of carboxymethyl cellulose in polyethylene glycol. In the suspensions the carboxymethyl cellulose is in the form of a finely divided solid. Preferably, the particle size distribution is such that about 80% of the particles have a size less than about 75 $\mu$m.

Carboxymethyl cellulose is usually available commercially in the form of its sodium salt. Both technical and purified grades of carboxymethyl cellulose may be used in the toothpastes of this invention.

Although any water-miscible, liquid polyethylene glycol may be used in the fluidized polymer suspensions, the preferred ones are those with molecular weight less than about 1,000. More preferred are those with molecular weight less than about 700, and most preferred those with molecular weight of about 200 to about 400.

Hydrated thickening silica is incorporated in the fluidized polymer suspensions of this invention to serve as a suspending agent for the dispersed water-soluble polymer. Hydrated thickening silicas are synthetic silicas comprising fumed silicas, amorphous precipitated silicas and gel silicas. The preferred hydrated thickening silicas, also known as thickening silicas, are colloidal gel silicas. More preferred ones are Aerosil™ 200 silica, available from Degussa AG, Frankfurt, Germany, and Syloblanc™ 34 silica, available from Grace Davison S. A., Epernon, France. The most preferred is Aerosil™ 200 silica.

In the fluidized polymer suspensions used in this invention it is preferred that the carboxymethyl cellulose be present at a minimum level of about 20% based on the total weight of the fluidized polymer suspension. More preferably the minimum level is about 40%, and most preferably about 45%. It is preferred that the maximum level of carboxymethyl cellulose be about 80%, more preferably about 60% and most preferably about 55%.

Preferably the maximum level of polyethylene glycol used in the fluidized polymer suspension is about 80% by weight based on the total weight of the fluidized polymer suspension. More preferably the maximum level is about 60%, and most preferably about 55%. A preferred minimum level of polyethylene glycol is about 20%, more preferred about 40%, and most preferred about 45%.

The maximum level of hydrated thickening silica that is used in the fluidized polymer suspension is about 3% by weight based on the total weight of the fluidized polymer suspension. Preferably the maximum is about 2%. The minimum level of hydrated silica is about 0.5%. The level of hydrated silica that is chosen for use in the fluidized polymer suspension depends on the particular balance of viscosity, fluidity and stability that is desired. At the lower levels, ca. 0.5%, high fluidity and low viscosity are achieved, but stability, as judged by phase separation, is not as good as that achieved at the higher levels, i.e. ca. 2%. A good compromise of fluidity, viscosity and stability has been achieved at intermediate levels of about 1.5 wt. %.

A preferred fluidized polymer suspension for use in this invention comprises from about 45 to about 55 wt. % carboxymethyl cellulose, from about 55 to about 45 wt. % polyethylene glycol having a molecular weight of about 400, and from about 0.5 to about 2 wt. % Aerosil™ 200 hydrated thickening silica.

Another class of ingredients present in the toothpastes of this invention are humectants, which are used to retain moisture, particularly at the nozzle end of the toothpaste tube where the toothpaste can be in prolonged contact with air. Typical humectants for use in the toothpastes of this invention include glycerin, sorbitol, polyethylene glycol, propylene glycol or mixtures thereof, which are mixed with a suitable humectant vehicle such as water.

The dental abrasives for use in the toothpastes of this invention are typically silicas and insoluble inorganic salts. Preferred inorganic salts are calcium carbonate, dibasic calcium phosphate, tribasic calcium phosphate, calcium sulfate, insoluble sodium metaphosphate, hydrated aluminum oxide, and magnesium carbonates and phosphates. Silicas and silica xerogels are particularly useful for translucent or transparent toothpastes.

The amounts of the various ingredients present in the toothpastes of this invention are quite variable and depend on the exact properties desired in the final product. In particular, the ingredient amounts may vary widely depending whether the toothpaste is a cream or a gel type.

The amount of abrasive is limited only by the amount which safely provides good polishing and cleaning and when combined with the other ingredients gives toothpaste that is smooth and flowable with acceptable taste and minimum grittiness. The minimum amount of abrasive used is about 5% by weight based on the total weight of the toothpaste. Preferably the minimum amount is about 7%, and more preferably about 10%. The maximum amount of abrasive used is about 45%, preferably about 30%, and more preferably about 25%.

The maximum level of humectant present in the toothpastes of this invention is about 85% by weight based on the total weight of the toothpaste. Preferably the maximum level is about 80%, and more preferably about 75%. The minimum level present in the toothpaste is about 15%. Preferably the minimum level is about 20%, and more preferably about 25%.

The amount of water used is preferably from about 5 to about 45% by weight based on the total weight of the toothpaste, and more preferably from about 5 to about 40 wt. %.

The toothpastes will contain fluidized polymer suspension in an amount sufficient to provide carboxymethyl cellulose at a preferred minimum level of about 0.1 wt. % based on the total weight of the toothpaste formulation. A more preferred minimum level is about 0.2 wt. %, and the most preferred minimum level is about 0.3 wt. %. The maximum level of carboxymethyl cellulose provided by the fluidized polymer suspension is preferably about 5 wt. % based on the total weight of the toothpaste formulation. A more preferred maximum is about 3 wt. %, and the most preferred maximum about 2 wt. %.

The toothpaste formulations of this invention may contain additional ingredients, for example: anionic, cationic, nonionic and ampholytic surfactants, especially anionic surfactants having detergent and foaming properties; coloring agents; whitening agents; preservatives; and antibacterial agents. Any of these additives can be present in the toothpaste of this invention in an amount up to about 5%. Typical anionic surfactants include sodium lauryl sulfate and sodium n-lauroyl sarcosinate, and typical nonionic surfactants include block copolymers of ethylene oxide and propylene oxide wherein the ratio of ethylene oxide units to propylene oxide units is 2:1. Suitable flavoring agent include oils of peppermint, spearmint and cinnamon. Sweetening agents such as sodium saccharin, preservatives such as p-chlorophenyl biguanide, 4-chlorobenzhydryl biguanide and 5,6-dichloro-2-guanidinobenzimidazole can also be included in the compositions of this invention.

In addition the compositions of this invention can contain a fluorine containing compound in an amount sufficient to provide up to about 1,000 ppm fluoride ion content. Typical fluorine containing compounds include sodium fluoride or sodium monofluorophosphate.

In the process for preparing the toothpastes of this invention the first step is the preparation of the fluidized polymer suspension of carboxymethyl cellulose. In the preparation of the fluidized polymer suspensions, the polyethylene glycol is added to a high shear mixing device, and then the appropriate hydrated silica is added. The mixture is stirred for a sufficient time to swell the silica, and then the carboxymethyl cellulose is added. Further stirring is carried out until suspension is complete. It is preferred that the temperature of the reaction mixture is maintained below 40° C. during the preparation.

For preparation of the toothpastes, the fluidized polymer suspension is stirred with: a) humectant or a mixture of humectants; b) humectant vehicle, most typically water; c) salts; d) abrasive; and e) flavors, colorants and surfactants to obtain a complete toothpaste formulation. In a preferred method of preparation, the fluidized polymer suspension is added directly to the mixture of humectants and humectant vehicle and stirred until the polymer particles are fully dissolved; then any salts are added, followed by abrasive. The abrasive is added after complete dissolution of the salts. The mixture is stirred until the particles of abrasive are wetted out; then the flavors are added, followed by surfactant.

This invention is illustrated by the following examples, which are for illustration and not intended to be limiting. All percentages, parts, etc., are by weight unless otherwise indicated.

EXAMPLES 1–5

These examples illustrate the preparation of fluidized polymer suspensions utilizing carboxymethyl cellulose (CMC 9H4XF, available from Hercules Incorporated, Wilmington, Delaware), polyethylene glycol 400 (PEG 400, available from Dow Benelux N. V., Edegem, Belgium) and two different hydrated thickening silicas, Aerosil™ 200 (Degussa AG, Frankfurt, Germany) and Syloblanc™ 34 (Grace Davison S. A., Epernon, France).

The PEG 400 was added to a high shear mixing device (Waring Blender/Mixer) and then the appropriate hydrated thickening silica was added. The resulting mixture was stirred at high rate for sufficient time, about 10 minutes, to swell the silica, and then the carboxymethyl cellulose was added. Stirring was continued for an additional 10 minutes. Temperature during the preparation was maintained below 40° C.

The compositions of the fluidized polymer suspensions of Examples 1–5 are summarized in Table 1.

The suspensions were characterized by Brookfield viscosity (LVF spindle 4 and 30 rpm), fluidity and stability over a 3 month period. The data are in Table 2. The fluidity was evaluated by measuring the time required for the free flow of 50 ml of suspension through an orifice using a modification of ASTM D1200, but utilizing a slightly different size cup (AFNOR cup No. 6). In the test, the cup orifice is closed by holding a rubber stopper against it. Then the cup is filled with the prepared fluid, the preferred method being to overfill the cup and then scrape off the excess with a straight-edge. The stopper is pulled away, and the time to fill a 50 ml. graduated cylinder is measured. The shorter the time, the better the fluidity.

To simulate 1 year stability at room temperature, the suspensions were aged for 3 months at 40° C., and the stability was characterized by the extent of phase separation. After 3 months of aging (both at room temperature and at 40° C.) the stability was characterized by weighing the amount of clear syneresis layer, if any, on top of the suspension and expressing it as the percent of total weight of the suspension sample. These data are presented as "Syneresis Layer (Wt. %)" in Table 2.

In another method for measuring syneresis, glass flasks (100 ml) were filled to a 50 mm height with fluidized polymer suspension and then stored at room temperature and at 40° C. After 1 day, 7 days, 30 days and 3 months, the height of the clear layer, if any, was measured. The results are reported in Table 2. They are expressed as: height of syneresis (mm)/original height (50 mm). For example 0.5/50 means 0.5 mm syneresis, 50 mm original height. The term "Film" means a non-measurable thin clear layer.

TABLE 1

FLUIDIZED POLYMER SUSPENSIONS

| Ingredients | Example 1 | Example 2 | Example 3 | Example 4 | Example 5 |
|---|---|---|---|---|---|
| PEG 400 | 53% | 53% | 54% | 54.5% | 53.5% |
| Aerosil 200 | 2 | — | 1 | 0.5 | 1.5 |
| Syloblanc 34 | — | 2 | — | — | — |
| 9H4XF CMC | 45 | 45 | 45 | 45 | 45 |

TABLE 2

CHARACTERIZATION OF FLUIDIZED POLYMER SUSPENSIONS

| | Example 1 | Example 2 | Example 3 | Example 4 | Example 5 |
|---|---|---|---|---|---|
| 50 ml Flow (sec, Cup 6) | | | | | |
| 0 | Poor Flow | 102 | 116 | 62 | 82 |
| 24 hours | 106 | 64 | 83 | 51 | 73 |
| 1 week | 97 | 54 | 65 | 42 | 73 |
| 1 month | 102 | 50 | 59 | 45 | 64 |
| 3 months | 95 | 58 | 66 | — | — |
| LVF Brookfield Viscosity Spindle 4, 30 rpm (cps) | | | | | |
| 0 | 7,400 | 6,600 | 4,600 | 3,040 | 4,000 |
| 24 hours | 4,800 | 3,500 | 3,400 | 2,300 | 3500 |
| 1 week | 4,300 | 3,000 | 3,380 | 2,300 | 3,400 |
| 1 month | 4,500 | 2,820 | 3,100 | 2,100 | 2,900 |
| 3 months | 4,300 | 3,060 | 3,360 | — | — |
| Syneresis Layer (Wt. %) | | | | | |
| 3 months, room temp. | 1.5 | 9.7 | 3.7 | — | — |
| 3 months, 40° C. | 2.5 | 11 | 5.8 | — | — |
| Syneresis (mm) | | | | | |
| 24 hrs, room temp. | 0 | 0 | 0 | 0 | 0 |
| 24 hrs., 40° C. | 0 | 0 | 0 | Film | 0 |
| 1 week, room temp. | 0 | 0.5/50 | 0 | 0 | 0 |
| 1 week, 40° C. | 0 | 2/50 | Film | 5/50 | 0 |
| 1 month , room temp. | 0 | 4/50 | 0 | 5/50 | Film |
| 1 month, 40° C. | Film | 4/50 | 2/50 | 6/50 | 0.5/50 |
| 3 months, room temp. | 0.5/50 | 4/50 | 2/50 | — | — |
| 3 months, 40° C. | 0.5/50 | 5/50 | 2/50 | — | — |

The data indicate that incorporating 2% hydrated thickening silica into the system (Examples 1 and 2) gives very viscous suspensions at the time of preparation. However, more than a 35% viscosity drop is observed after 24 hours. Decreasing the amount of the hydrated thickening silica from 2% to 1% and 0.5% (Examples 3 and 4) yielded more fluid suspensions; however, their stability was not good (phase separation occurring after 1 week at 40° C.). The Aerosil™ 200 thickening silica gave thicker and more stable suspensions than Syloblanc™ 34.

EXAMPLE 6 AND COMPARATIVE EXAMPLE A

Example 6 illustrates the preparation of a cream toothpaste using a fluidized polymer suspension prepared from 9M31XF CMC, available from Hercules Incorporated, Wilmington, Del., by the method used in Example 5. Comparative Example A illustrates preparation of the same toothpaste utilizing dry carboxymethyl cellulose in place of the fluidized polymer suspension, at a level equivalent to the amount of carboxymethyl cellulose present in the fluidized polymer suspension in Example 6.

The ingredients utilized are in Table 3. In Comparative Example A, the dry carboxymethyl cellulose (CMC) was added to glycerin in a glass mixer and mixed for 5 minutes. This is referred to as the "dispersion" step. Then the water and sorbitol were added, and mixing was continued for 30 minutes at 600 rpm. Viscosity was measured every 10 minutes. This is referred to as the "premix". The caustic and the salts were then added and mixing continued for 10 minutes. The mixture was then transferred to a Ross mixer; the silica and $TiO_2$ were added, and the resulting mixture was stirred briefly until the particles were wetted out. Then vacuum was applied and mixing at 60 rpm was continued for 15 minutes. Flavor was added followed by mixing for 5 minutes at 60 rpm, and then the surfactant was added followed by mixing for 10 minutes at 15 rpm under vacuum.

In Example 6, the dispersion step was bypassed by adding the fluidized polymer suspension (FPS) directly to the mixture of glycerin, sorbitol and water, and then the viscosity was measured every 5 minutes. The rest of the ingredients were then added as described above for the Comparative Example.

TABLE 3

Toothpaste Formulations
Cream Toothpastes

| Ingredients | Example 6 | Comparative Example A |
|---|---|---|
| Glycerin | 8.30% | 10.00% |
| CMC, dry (9M31XF) | — | 1.40 |
| Water | 39.15 | 39.15 |
| Sorbitol | 25.00 | 25.00 |
| FPS (45% 9M31XF CMC) | 3.1 | — |
| Sodium monofluoro- phosphate | 0.85 | 0.85 |
| Sodium saccharinate | 0.20 | 0.20 |
| NaOH (50%) | 0.40 | 0.40 |
| Syloblanc 81 abrasive hydrated silica | 20.00 | 20.00 |
| $TiO_2$ | 0.50 | 0.50 |
| Flavor | 1.00 | 1.00 |
| Sodium lauryl sulfate, dry powder | 1.50 | 1.50 |

The product toothpaste compositions were evaluated on the basis of their appearance, stability, viscosity and ribbon stand-up. The data are in Table 4.

Ribbon Stand-up is a measure of the anti-sag behavior of the toothpaste when it is squeezed from the tube. It characterizes the ability of the paste to maintain a circular ribbon shape on the brush.

TABLE 4

Toothpaste Properties
Cream Toothpaste

| | Example 6 | Comparative Example A |
|---|---|---|
| Premix Viscosity (cps), Helipath, Spindle TA, 20 rpm | | |
| 5 min | 5,850 | — |
| 10 min | 5,800 | 4,000 |
| 15 min | 5,600 | — |
| 20 min | 5,450 | 4,750 |
| 30 min | 5,200 | 4,850 |
| Toothpaste Viscosity (cps), Helipath, Spindle E, 5 rpm | | |
| 0 | 350 | 265 |
| 24 hours | 460 | 410 |
| 1 week | 550 | 475 |
| 2 weeks | — | 545 |
| 1 month | — | — |
| Freeze/Thaw Stability (cps) | | |
| 1 cycle | 415 | 375 |
| 2 cycles | 460 | 400 |
| 3 cycles | 460 | 420 |
| Toothpaste Appearance | | |
| 24 hours | S,G | S,G |
| 1 week | S,G | S,G |
| 2 weeks | — | S,G |
| 1 month | — | — |
| Ribbon Stand-up | | |
| 24 hours | Excellent | Excellent |
| 1 week | Excellent | Excellent |
| 2 weeks | — | Excellent |
| 1 month | — | — |
| Toothpaste Stability, Syneresis | | |
| 24 hours | T–,W– | T–,W– |
| 1 week | T–,W+ | T–,W+ |
| 2 weeks | — | T–,W+ |
| 1 month | — | — |

S = smooth toothpaste appearance
G = glossy toothpaste appearance
T–/T+= absence/presence of syneresis on top of storage flask
W–/W+= absence/presence of syneresis on walls of storage flask The data indicate that the fluidized polymer suspension dissolves faster in the sorbitol/water mixture than does the dry powder, even when the latter is predispersed in glycerin. Before complete dissolution, the dry powder goes through several dispersion steps during which the polymer agglomerates. The agglomeration is characterized by partially or fully swollen polymer. As solvation proceeds further, there is an increase in the viscosity, and as solvation continues, the gels begin to disaggregate, leading to a partially dispersed state characterized by a sharp decrease in the viscosity to a level about equivalent to what is observed with the fluidized polymer. On this basis, it is concluded that the fluidized polymer suspension dissolves rapidly, leading to a high viscosity within about 5 minutes, while the dry carboxymethyl cellulose requires about 30 minutes to reach the same state of hydration, as indicated by viscosity.

There were no significant differences in the properties of toothpastes made from dry carboxymethyl cellulose or fluidized polymer suspension. Except for viscosity, all properties were the same: good stability (no syneresis), very good ribbon stand-up, and smooth, glossy appearance.

EXAMPLE 7 AND COMPARATIVE EXAMPLE B

Example 7 illustrates the preparation of a gel toothpaste using a fluidized polymer suspension prepared by the method of Example 5 from 9M31XF CMC, available from Hercules Incorporated, Wilmington, Del. Comparative Example B illustrates preparation of the same toothpaste utilizing dry 9M31XF carboxymethyl cellulose in place of the fluidized polymer suspension at a level equivalent to that of the carboxymethyl cellulose present in the fluidized polymer suspension in Example 7.

The ingredients utilized are in Table 5. In Comparative Example B, the dry carboxymethyl cellulose (CMC) was added to the polyethylene glycol in a glass mixer and mixed for 5 minutes at 600 rpm. The remainder of the steps were the same as those described above for Comparative Example A. In Example 7, the dispersion step was bypassed by adding the fluidized polymer suspension (FPS) directly to the mixture of polyethylene glycol, sorbitol and water. The remainder of the steps were as described above for Example 6. Stirring was continued until the particles of silica were wetted out. Then vacuum was applied and mixing at 60 rpm was continued for 15 minutes. Colorant was added followed by mixing for 15 minutes, and then the flavor and surfactant were added followed by mixing for 15 minutes and 10 minutes respectively at 5 rpm under vacuum.

The data on evaluation of the toothpastes are presented in Table 6.

TABLE 5

Toothpaste Formulations
Gel Toothpastes

| Ingredients | Example 7 | Comparative Example B |
|---|---|---|
| Polyethylene Glycol 400 | 3.52% | 4.00% |
| Water | 8.15 | 8.15 |
| Sorbitol | 68.00 | 68.00 |
| CMC, dry (9M31XF) | — | 0.40 |
| FPS (45% 9M31XF CMC) | 0.89 | — |
| Sodium monofluorophosphate | 0.75 | 0.75 |
| Sodium saccharinate | 0.20 | 0.20 |
| Sodium benzoate | 0.10 | 0.10 |
| Sident 15 hydrated silica | 15.00 | 15.00 |
| Colorant | 0.20 | 0.20 |
| Flavor | 0.70 | 0.70 |
| Sodium lauryl sulfate, liquid | 2.50 | 2.50 |

TABLE 6

Toothpaste Properties
Gel Toothpaste

| | Example 7 | Comparative Example B |
|---|---|---|
| Premix Viscosity (cps), Helipath, spindle TA, 20 rpm | | |
| 5 min | 2,050 | — |
| 10 min | 2,350 | 2,300 |
| 15 min | — | — |
| 20 min | 2,250 | 2,200 |
| 30 min | 2,050 | 2,150 |
| Toothpaste Viscosity (cps), Helipath, spindle E, 5 rpm | | |
| 0 | 345 | 355 |
| 24 hours | 415 | 430 |
| 1 week | 515 | 520 |
| 2 weeks | 530 | 555 |
| 1 month | 545 | 550 |
| Freeze/Thaw Stability (cps) | | |
| 1 cycle | 360 | 380 |
| 2 cycles | 385 | 385 |
| 3 cycles | 380 | 385 |
| Toothpaste Appearance | | |
| 24 hours | Tr,S,G | Tr,S,G |
| 1 week | Tr,S,G | Tr,S,G |
| 2 weeks | Tr,S,G | Tr,S,G |
| 1 month | Tr,S,G | — |

TABLE 6-continued

Toothpaste Properties
Gel Toothpaste

| | Example 7 | Comparative Example B |
|---|---|---|
| Ribbon Stand-up | | |
| 24 hours | Excellent | Excellent |
| 1 week | Excellent | Excellent |
| 2 weeks | Excellent | Excellent |
| 1 month | Excellent | Excellent |
| Toothpaste Stability, Syneresis | | |
| 24 hours | T–,W– | T–,W– |
| 1 week | T–,W– | T–,W– |
| 2 weeks | T–,W– | T–,W– |
| 1 month | T–,W– | T–,W– |

As in the case of preparation of the cream toothpaste (Example 6 and Comparative Example A), the dry carboxymethyl cellulose was first dispersed in polyethylene glycol, and then the sorbitol/water mixture was added and the resulting mixture mixed for 30 minutes before addition of the remaining ingredients. When fluidized polymer suspension was utilized, it was poured into the polyethylene glycol/sorbitol/water mixture without any predispersion.

In gel toothpastes, because of the lower water content, dispersion/disaggregation of the binder/thickener presents less risk of lump formation. The data here confirm this, demonstrating that both the fluidized polymer suspension and the dry carboxymethyl cellulose develop similar viscosities. However, it was also observed that the fluidized polymer suspension gave a more transparent gel premix after only 10 minutes mixing, while the dry powder required about 20 minutes to achieve similar transparency.

The dry carboxymethyl cellulose and the fluidized polymer suspension produced toothpastes having similar viscosity, freeze/thaw stability, appearance, ribbon stand-up and lack of syneresis.

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. A fluidized polymer suspension comprising carboxymethyl cellulose, polyethylene glycol and hydrated thickening silica.

2. The fluidized polymer suspension of claim 1 wherein the polyethylene glycol has a molecular weight less than about 1,000.

3. The fluidized polymer suspension of claim 1 wherein the polyethylene glycol has a molecular weight less than about 700.

4. The fluidized polymer suspension of claim 1 wherein the polyethylene glycol has a molecular weight of from about 200 to about 400.

5. The fluidized polymer suspension of claim 1 wherein the particle size distribution of the carboxymethyl cellulose is such that about 80% of the particles have a size less than about 75 μm.

6. The fluidized polymer suspension of claim 1 containing from about 20 to about 80 wt. % polyethylene glycol, from about 20 to about 80 wt. % carboxymethyl cellulose, and from about 0.5 to about 3 wt. % hydrated thickening silica.

7. The fluidized polymer suspension of claim 1 containing from about 40 to about 60 wt. % polyethylene glycol, from about 40 to about 60 wt. % carboxymethyl cellulose, and from about 0.5 to about 2 wt. % hydrated thickening silica.

8. The fluidized polymer suspension of claim 1 containing from about 45 to about 55 wt. % polyethylene glycol, from about 45 to about 55 wt. % carboxymethyl cellulose, and from about 0.5 to about 2 wt. % hydrated thickening silica.

9. The fluidized polymer suspension of claim 1 containing from about 20 to about 80 wt. % carboxymethyl cellulose having a particle size distribution such that about 80% of the particles have a size less than about 75 μm, from about 20 to about 80 wt. % polyethylene glycol of molecular weight less than about 1,000, and from about 0.5 to about 3 wt. % hydrated thickening silica.

10. In a process for preparing a toothpaste composition comprising carboxymethyl cellulose, the improvement comprising substituting for dry, solid carboxymethyl cellulose, and the fluidized polymer suspension of claim 1.

11. The process of claim 10 wherein the carboxymethyl cellulose present in the fluidized polymer suspension dissolves in the toothpaste composition in a shorter time than does the dry, solid carboxymethyl cellulose.

12. The process of claim 10 wherein the polyethylene glycol has a molecular weight less than about 1,000.

13. The process of claim 10 wherein the polyethylene glycol has a molecular weight less than about 700.

14. The process of claim 10 wherein the polyethylene glycol has a molecular weight of from about 200 to about 400.

15. The process of claim 10 wherein the toothpaste composition further comprises water and humectant selected from the group consisting of glycerin, sorbitol, propylene glycol, polyethylene glycol and mixtures thereof.

16. The process of claim 10 wherein the particle size distribution of the carboxymethyl cellulose in the fluidized polymer suspension is such that about 80% of the particles have a size less than about 75 μm.

17. The process of claim 10 wherein the fluidized polymer suspension comprises from about 20 to about 80 wt. % polyethylene glycol, from about 20 to about 80 wt. % carboxymethyl cellulose, and from about 0.5 to about 3 wt. % hydrated thickening silica.

18. The process of claim 10 wherein the fluidized polymer suspension comprises from about 40 to about 60 wt. % polyethylene glycol, from about 40 to about 60 wt. % carboxymethyl cellulose, and from about 0.5 to about 2 wt. % hydrated thickening silica.

19. The process of claim 10 wherein the fluidized polymer suspension comprises from about 45 to about 55 wt. % polyethylene glycol, from about 45 to about 55 wt. % carboxymethyl cellulose, and from about 0.5 to about 2 wt. % hydrated thickening silica.

20. The process of claim 15 wherein the toothpaste composition comprises from about 5 to about 45 wt. % dental abrasive, from about 15 to about 85 wt. % humectant, and from about 5 to about 45 wt. % water, and wherein the fluidized polymer suspension is used in an amount sufficient to provide from about 0.1 to about 5 wt. % carboxymethyl cellulose.

21. The process of claim 15 wherein the toothpaste composition comprises from about 10 to about 25 wt. % dental abrasive, from about 25 to about 75 wt. % humectant, from about 5 to about 40 wt. % water, and wherein the fluidized polymer suspension is used in an amount sufficient to provide from about 0.3 to about 2 wt. % carboxymethyl cellulose.

22. The process of claim 20 wherein the fluidized polymer suspension comprises from about 40 to about 60 wt. % polyethylene glycol, from about 40 to about 60 wt. %, carboxymethyl cellulose, and from about 0.5 to about 3 wt. % hydrated thickening silica.

23. The process of claim 20 wherein the humectant comprises a member selected from the group consisting of sorbitol, glycerin, polyethylene glycol, propylene glycol and mixtures thereof.

24. The process of claim 23 wherein the polyethylene glycol contained in the fluidized polymer suspension has a molecular weight of from about 200 to about 400.

25. The process of claim 10 wherein the toothpaste composition further comprises ingredients selected from the group consisting of flavors, sweeteners, preservatives, surfactants, antibacterials, coloring agents and fluoride.

26. Toothpaste made by the process of claim 10.

27. Toothpaste made by the process of claim 20.

28. A toothpaste composition comprising dental abrasive, humectant and the fluidized polymer suspension of claim 1.

29. The toothpaste composition of claim 28 wherein the polyethylene glycol contained in the fluidized polymer suspension has a molecular weight less than about 1,000.

30. The toothpaste composition of claim 28 wherein the humectant comprises a member selected from the group consisting of glycerin, sorbitol, propylene glycol, polyethylene glycol and mixtures thereof.

31. The toothpaste composition of claim 28 further comprising water.

* * * * *